(12) United States Patent
Fresco

(10) Patent No.: US 6,524,243 B1
(45) Date of Patent: Feb. 25, 2003

(54) TONOMETER INCORPORATING AN ELECTRICAL MEASUREMENT DEVICE

(75) Inventor: Bernard B. Fresco, Toronto (CA)

(73) Assignee: Jordan Technology Inc., Tortola (VG)

( * ) Notice: Subject to any disclaimer, the term of this patent is extended or adjusted under 35 U.S.C. 154(b) by 0 days.

(21) Appl. No.: 09/678,799

(22) Filed: Oct. 4, 2000

(51) Int. Cl.[7] ............................................. A61B 3/18
(52) U.S. Cl. ............................................. 600/399
(58) Field of Search ........................ 600/399, 558, 600/561, 398, 404, 405; 73/1.62, 753; 324/130; 330/9, 284; 702/139, 87; 250/214 A

(56) References Cited

U.S. PATENT DOCUMENTS

| | | |
|---|---|---|
| 1,637,421 A | 8/1927 | Lipschutz |
| 1,661,718 A | 3/1928 | Davis |
| 2,656,715 A | 10/1953 | Tolman ........................ 73/80 |
| 2,882,891 A | 4/1959 | Husted ........................ 128/2 |
| 2,984,099 A | 5/1961 | Tolman ........................ 73/80 |
| 3,992,926 A | 11/1976 | Berryhill ...................... 73/80 |
| 4,505,278 A | 3/1985 | Alban ........................ 128/774 |
| 4,622,459 A * | 11/1986 | Bouge et al. ............. 250/214 A |
| 4,747,296 A * | 5/1988 | Feldon et al. ............... 600/558 |
| 5,176,139 A | 1/1993 | Fedorov et al. ............. 128/645 |
| 5,197,473 A | 3/1993 | Fedorov et al. ............. 128/645 |
| 5,836,873 A | 11/1998 | Fresco ........................ 600/398 |

FOREIGN PATENT DOCUMENTS

| | | | |
|---|---|---|---|
| EP | 0584929 | 7/1993 | ............ A61B/3/16 |
| FR | 2542603 | 3/1983 | ............ A61B/3/16 |
| SU | 457466 | 1/1975 | ............ A61B/3/16 |
| SU | 2004187 | 9/1992 | ............ A61B/3/16 |
| WO | WO 97/43946 | 11/1997 | ............ A61B/3/16 |

* cited by examiner

Primary Examiner—Max F. Hindenburg
Assistant Examiner—Brian Szmal
(74) Attorney, Agent, or Firm—Bereskin & Parr

(57) ABSTRACT

An applanation tonometer, for measuring pressure within a human eye, the tonometer comprising an electrical measurement apparatus which detects the mechanical displacement of a plunger, the displacement of the plunger provided by means applied pressure to the eye, the electrical measurement apparatus converting the corresponding mechanical displacement of the plunger into an electrical signal, the electrical signal corresponding to ocular pressure within the eye and displayed on an electrical display device.

18 Claims, 11 Drawing Sheets

TONOMETER INCORPORATING AN ELECTRICAL MEASUREMENT DEVICE

FIELD OF THE INVENTION

This invention relates to an apparatus for and a method of measuring intraocular pressure in the human eye. This invention more particularly relates to an applanation tonometer comprising electrical sensor circuitry for measuring such intraocular pressure in the human eye.

BACKGROUND OF THE INVENTION

It is well known that excessive internal pressure within the human eyeball is a component of glaucoma, a disease of the eye. This disease accounts for a significant percentage of all blindness. Surveys have shown it to be present and unrecognized in a significant number of people, particularly people over the age of 40 and even more so for people over the age 50.

It is also known that where the presence of glaucoma can be identified at an early stage, damage to the eye and subsequent blindness can be arrested. Appropriate medication and surgery can serve to arrest the progress of the disease so that useful vision is retained.

In view of the fact that glaucoma is widespread, numerous proposals have been made for measuring the internal eyeball pressure. Many of these are complex precision instruments, which are expensive, and which require elaborate clinical settings for their operation. Typically, such instruments apply an amount of force to the eyeball, sufficient to allow an objective measurement of specific flattening (applanation) or indenting (indentation) of the surface of the eye. The amount of force required to achieve a certain applanation or indentation is correlated with the intraocular pressure measured internally, and usually expressed in mm of mercury.

Conventionally, the clinical instrument involved has some element which is applied directly to the cornea of the open eye to measure the applanation or indentation of the cornea. In view of natural human reflexes, this requires a topical anesthetic. The equipment is complex and costly and requires a trained and sophisticated technician to operate it. Other proposals have been made, and the following patents list proposals known to the applicant: U.S. Pat. Nos. 1,637,421; 1,661,718; 2,656,715; 5,176,139; and 5,197,473; French Patent 2,542,603; and Russian Federation Patents 2,004,187 and 457,466.

The Lipschutz U.S. Pat. No. 1,637,421 is a pressure indicator. It is not concerned with measuring eyeball pressure, but rather it is concerned with applying pressure to other parts of the human body. It is based on the well known phenomenon that sensitivity to pressure of an area of the body is an indication of disease. More particularly, it relies on the fact that the progress of the disease is related to the sensitivity of an associated area of the body. As such, it provides a device enabling the pressure applied to a particular area to be measured, so this pressure can be correlated with the progress of the disease. No clear directions are given, with regard to applying this technique to the human eye. Measuring pressure in the human eye presents unique and difficult problems, as compared to other parts of the anatomy. As the human eye is sensitive and delicate, everyone has a strong, natural reflex to close their eyes, if any attempt is made to touch the eye. This Lipschutz patent does not address this issue.

A hardness testing device is disclosed in U.S. Pat. No. 1,661,718 which is of marginal relevance.

An ocular tension indicator is disclosed in the Tolman U.S. Pat. No. 2,656,715. However, this requires the eyeball to be contacted. It relies upon relative axial displacement of different components of known, set weight, to determine the pressure within the eye. As such, it appears to be a delicate, precision instrument. Since it must contact the naked eye, it cannot be used outside of a clinical setting.

The two Fedorov U.S. Pat. Nos. 5,176,139 and 5,197,473 disclose an ocular tonometer and a related method. This relies on a somewhat unique technique where a ball is permitted to fall freely onto an eyelid-covered cornea. The kinetic energy of the ball deforms a cornea. The amount of the ball rebound varies depending upon the amount of intraocular pressure and this is judged against the height of the ball rebound. This technique would appear difficult to carry out, since it depends upon judging the height of the ball rebound.

Russian Patent 457,466 discloses an intraocular pressure transducer. This relies upon a Hall effect generator. Weights determine the penetration force of a plunger, whose displacement is sensed by the Hall effect generator with an output proportional to the displacement. Russian Patent 2,004,187 discloses an eye tonometer having a hollow cylindrical body with tips and working end face surfaces. It is not clear how this device is intended to work. In any event, it is again intended to be applied to the naked eyeball, which again would require the application of a topical anesthetic in a clinical setting.

Now, one of the problems with measuring intraocular pressure is that it can vary during the course of the day, and even from hour to hour. Accordingly, it is highly desirable to provide some simple, inexpensive technique for measuring this pressure. This technique should enable an ordinary person to measure the intraocular pressure within their eyes, without requiring complex expensive equipment, without requiring attendance at a clinic or the like, and without requiring the time of highly trained clinical staff.

SUMMARY OF THE INVENTION

An applanation tonometer comprising: a main body; a plunger mounted in the main body for movement relative thereto and having a first end portion comprising a contact member for contacting an eyelid, the contact member being substantially planar and sufficiently large that, in use, the eyeball is flattened and subjected to applanation, and the plunger having a second end portion mounted in the main body; a transducer mounted between the plunger and the main body, for converting a load applied to the first end portion of the plunger into an electrical signal; an electrical display device connected to the transducer, for indicating the magnitude of the load applied to the first end portion of the plunger; wherein the plunger is slidably mounted within the main please send your reply to body; wherein a spring member is mounted between the plunger and the main body for providing a spring biasing force in relation to the displacement of the plunger relative to the main body, wherein the transducer includes a sensing device attached to the plunger, for conversion of the displacement of the plunger into the electrical signal, wherein the sensing device comprises an elongate member provided with a plurality of slot regions, and a plurality of blocking regions, alternating with one another, and wherein the transducer includes measurement means provided at a measurement location, for counting blocking regions and slot regions passing by the measurement location.

In accordance with another aspect of the present invention, a method of obtaining information concerning the pressure within the eyeball of the subject, is obtained by determining the load on the eyeball when a pressure phosphene is detected by the subject. The method further includes applying the load to the eyelid, so as to apply pressure through the eyelid to the eyeball. The load applied to the eyelid is progressively increased until the pressure phosphene is detected, terminating increasing the load when the pressure phosphene is detected, and noting the largest load applied to the eyelid as the load causing onset of the pressure phosphene.

The method of obtaining the load applied to the eyelid includes providing a tonometer including: a main body; a plunger slidably mounted within the main body and including a contact member at one end for contacting in the eyelid; a sensing device attached to the plunger and extending into the main body; an electrical measurement apparatus for detecting displacement of the sensing device; a spring member acting between the plunger and the housing, biasing the contact member away from the housing; a reset switch for resetting a previous reading indicative of the load; and an electrical display for displaying the applied pressure detected by the tonometer, the method comprising:

(a) resetting the tonometer by depressing the reset switch;
(b) locating the contact member of the plunger against the eyelid;
(c) displacing the main body of the tonometer towards the eyelid so as to displace the plunger into the main body against the action of the spring member, whereby the electrical measurement apparatus determines the displacement of plunger and the pressure detected by the tonometer;
(d) when the subject notices the pressure phosphene, terminating displacement with the main body and removing the tonometer; and
(e) reading the applied pressure magnitude from the display.

DETAILED DESCRIPTION OF THE DRAWINGS

For a better understanding of the present invention and to show more clearly how it may be carried into effect, reference will now be made, by way of example, to the accompanying drawings, which show preferred embodiments of a tonometer of the present invention, and in which.

DESCRIPTION OF PREFERRED EMBODIMENTS

Figure 1:
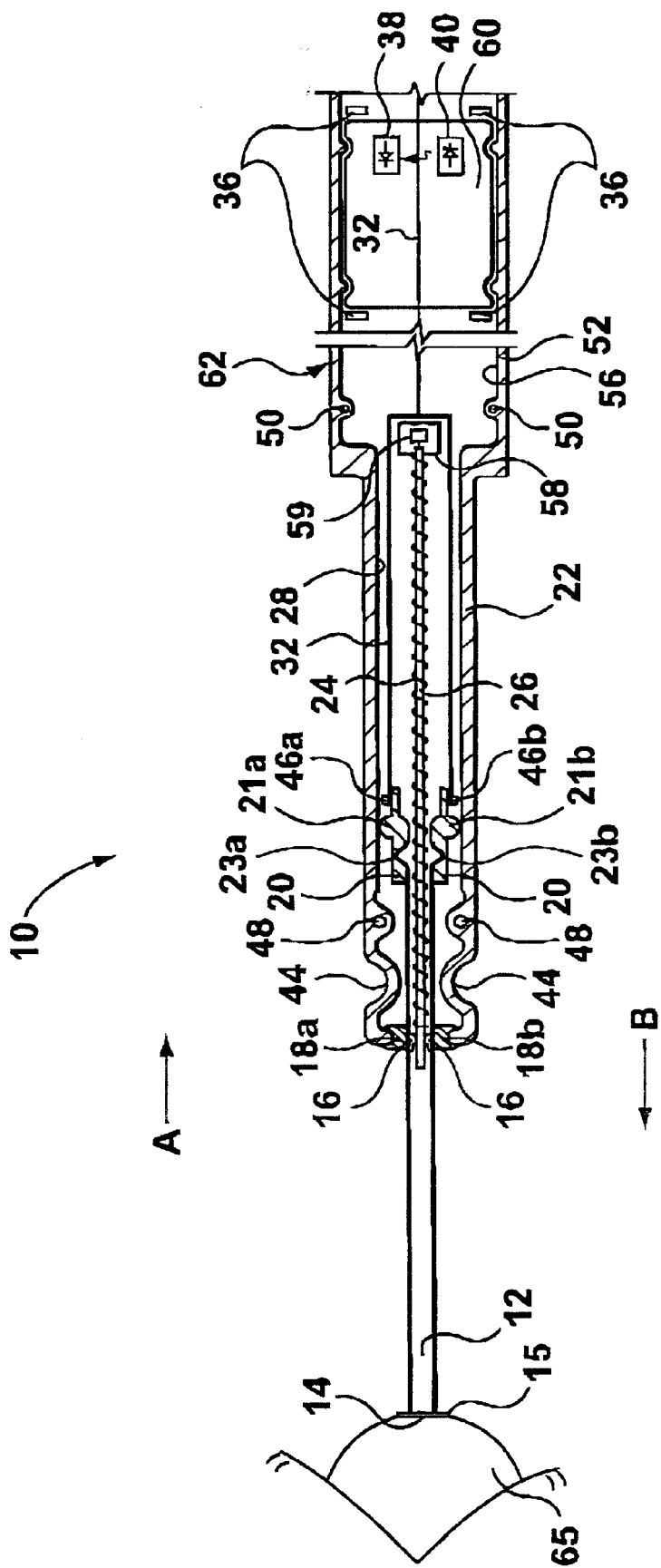
FIG. 1 illustrates a vertical cross sectional view of a first embodiment of a tonometer incorporating an electrical measurement apparatus.

FIG. 1 illustrates a cross sectional view of a tonometer 10 comprising an electrical measurement device 60. The tonometer 10 has a main body or housing 22. The left hand portion of the body 22 is essentially tubular and is adapted to be gripped and held by a user. For this purpose, the left hand portion of the main body 22 comprises an inwardly curved finger grip 44, to facilitate gripping of the device, and pressing of the device against a users eye, as detailed below.

The right hand portion of the body 22, as shown in the drawing, includes a housing 62 of increased cross section, where the cross section can be either rectangular or circular. The housing 62 comprises an outer casing 52 and a housing cavity 56 for holding electrical measurement apparatus 60 for generating an electrical measurement and readout of intraocular eye pressure.

The main body 22 defines an internal bore 28 extending from the left hand end of the main body 22 to the housing cavity 56 which holds the electrical measurement apparatus 60. The cross section of the internal bore 28 is generally circular and is such that a plunger 12 is free to move axially within the bore 28.

The plunger 12 extends out of the left hand end of the main body 22. The plunger 12 is supported for sliding movement relative to the main body 22 by means of a first bearing pair comprising an annular bearing member indicated at 18a, 18b located at the left hand end of the main body 22. The left hand end portion of the plunger includes a head or contact member 15 which can be any desired shape. It is preferred for it to present a flat, circular disk surface 14, i.e. as a conventional applanation tonometer. The profile to the right of the disk 14, as viewed in the drawing, is not critical. The right hand end of the plunger 12 attaches to a second bearing member 20, which comprises a pair of semi-circular annular channel regions 23a, 23b for receiving and retaining the right hand end of the plunger. The bearing member 20 further comprises an annular second bearing member, indicated at 21a, 21b. The length of the plunger extending between the contact member 15 and right end of the plunger is of uniform cross section and hollow. The first bearing member 18a, 18b and the second bearing member 21a, 21b provide axial support for the plunger 12 and allow the plunger 12 to move within the bore 28 with reduced frictional force, such that the frictional force is negligible in comparison to a force applied to the plunger 12 contact member 15.

The plunger further comprises an annular first protrusion member 16 located within a hollowed inner region of the plunger. The first protrusion member 16 engages a helical coil spring 24 mounted around a shaft 26. As the plunger moves inward with respect to the main body 22, the protrusion member 16 engages the left hand end of the helical coil spring 24, compressing the coil spring against a spring blocking member 59 located on the right hand end of the shaft 26. The spring blocking member 59 and shaft 26 are held in place by a fixing member 58 mounted on the housing 62. It will be appreciated that the present invention may incorporate a tension spring mechanism in place of the compression coil spring 24 shown in FIG. 1. In this configuration, the left hand end of the helical coil spring 24 is anchored or fixed to the left hand portion of the shaft 26, where the inward movement of the plunger 12 due to an applied pressure causes the protrusion member 16 to stretch the coil spring 24. As the pressure to the plunger is removed, the tension in the spring coil return the plunger to it's original position.

A sensing member 32 is elongate and is attached at one end to the second bearing member 20 by means of a pair of securing members 46a, 46b. The other end of the sensing member 32 extends axially along the main body 22 and into the housing cavity 56 which holds the electrical measurement apparatus 60. Thus, the plunger 12, the bearing member 20 and the sensory member 32 are integral and move as a unit within the bore 28 and housing cavity 56. Thus, in use, applying pressure to the plunger 12 contact member 15 causes the plunger 12, the second bearing member 20 and the attached sensing member 32 all to move axially inwards. The coil spring 24 is compressed in proportion to the inward pressure (see arrow A in FIG. 1) applied to plunger 12. Thus, the inward displacement of the sensing member 33 within the housing cavity 56 is proportional to the applied pressure and is detected by the electrical measurement apparatus 60. The electrical measurement apparatus 60 provides an electrical signal in proportion to the movement of the sensing member 32 with respect to the sensory devices 38, 40.

A plurality of support legs 36 are used to mount a display device (not shown) on the surface of the tonometer 10 housing 62. The electrical signal from the electrical measurement apparatus 60 generates a read out of pressure on the display device in proportion to the applied pressure to the plunger 12 contact member 15.

By removing the pressure from the plunger 12 contact member 15, the spring coil 24 returns the plunger 12 to its original position by applying an outward pressure (see arrow B in FIG. 1) on the first and second protrusion members 16,17 within the plunger 12.

The main body 22 may comprise two halves, wherein both halves are secured together by securing members 48 and 50. It will be appreciated that in accordance with the present invention, the securing members 48, 50 may include screws, snap on fittings or any other securing method for mating two complementary pieces. By removing the top half of the main body, access is provided to the electrical circuitry and mechanical components of the tonometer 10.

Figure 2:
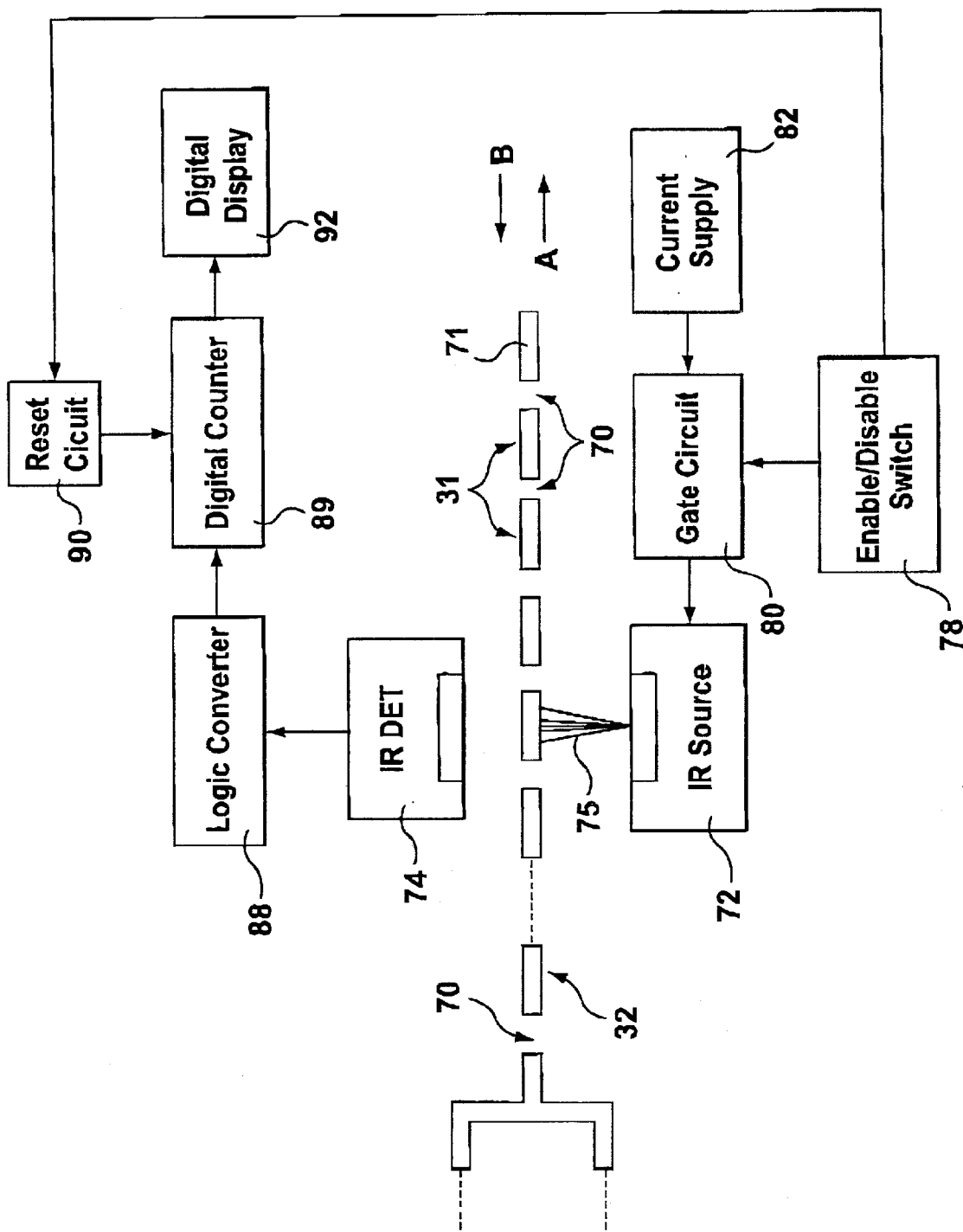
FIG. 2 illustrates a schematic view of the first embodiment of the electrical measurement apparatus of the tonometer of FIG. 1.

FIG. 2 illustrates a functional diagram of the electrical measurement apparatus 60 of the tonometer 10 shown in FIG. 1. FIG. 2 shows the sensing device 32 in more detail. The sensing device 32 includes a series of alternate slot regions or holes 70 separated by alternate blocking regions 31 (e.g. blackened card) fabricated or etched onto a plastic film or any other medium. The sensing device and the electrical measurement apparatus form a transducer for converting a load applied the contact member 15 located at the left hand end of the plunger into an electrical signal. The blocking regions between the slots are used to block an incident Infra Red (IR) optical signal 75 emitted from an optical IR LED source 72 (e.g. OP 165 by OPTEK), whereas the slots 70 pass the IR beam which is received by an Infra Red (IR) detector 74 (e.g. Photologic Sensors, OPL530 by OPTEK).

The IR LED source 72 is activated by a switch 78 that may be built into the finger grip 44 portion of the main body 22. Closing the switch 78 enables a gate circuit 80, which allows a current supply 82 to provide a constant current to the IR LED 72. The gate circuit 80 may be implemented as an analog switch. The gate circuit 80 and switch 78 are utilized in order to activate the IR LED 72 only when the user wishes to take Intraocular pressure measurements with the tonometer 10. This provides battery power savings for the electrical apparatus 60 to increase battery life. By activating the LED 72 with switch 78, a reset circuit 90 applies a reset signal to zero a digital counter device 88. The tonometer 10 digital display 92 will now give a zero reading.

Prior to applying pressure to the plunger 12, the right hand end 71 of the sensing member 32 will be located so as to block the activated LED's 72 Infra Red optical signal 75 from being detected by the IR detector 74. As pressure is increased on the plunger 12, the right hand end 71 of the sensing member 32 travels to the right and further into the housing 62 of the main body 22 as indicated by the direction of 'arrow A' shown in FIG. 2. Initial movement of the plunger 12 causes the IR Beam to encounter a slot or hole. The IR optical signal 75 passes through the slot and is detected by the IR optical detector 72 (see FIG. 3). Once the detector detects the beam, the detector output voltage is converted to a suitable logic high level (e.g. 5 V) by means of a logic convertor 88. As the plunger 12 continues to move, the IR beam encounters another blocked region on the sensing member 32 and the detector output voltage drops. The drop in voltage at the detector output 74 is converted to a logic low (e.g. 0 V) by the logic converter 88. Consequently, as the plunger 12 continues to move into the main body 22 (in the direction of arrow A), the logic converter output generates a series of pulses as result of the IR optical signal 75 being alternately blocked and passed through the sensing member 32. The series of pulses are applied to a digital counter device 89, whereby each pulse causes the counter to be incremented. The more the plunger 12 travels as result of applying pressure to it, the higher the count value registered in the counter 89. A display device 92 displays the counter value digitally.

As the pressure is removed from the plunger 12, the sensing member 32 travels back (direction of arrow B) to its initial position, whereby the right hand end 71 of the sensing member 32 returns to block the IR optical signal 75. A series of pulses is also generated as the sensing device moves in the direction of arrow B and back to its initial position. This is advantageous on the basis that for a given displacement of the plunger for a given pressure, the number of pulses generated by the logic converter 88 is doubled. The number of pulses for travel in the two different directions should be the same.

Once the measurement is completed and recorded, the switch 78 is activated a second time in order to disable the gate circuit 80 and cut off current flow from the current supply 82 to the LED source 72.

In use, the tonometer's 10 switch 78 is activated in order to reset the counter 89, reset the display 92 ( to read zero) and to turn on the IR LED source 72.

Then, the contact member 15 is brought up against the eyelid of a closed eye, this eyelid being indicated at 65. The contact member 15 is applied to the upper medial aspect of the eye, away from the cornea. This is done by the subject or user turning the eye out wards and slightly downwards. The eye can be either open or closed. The most convenient area may differ from person to person. The user just grasps the curved finger grip 44, to facilitate gripping of the device body 22 and places the circular surface 14 against the eyelid 65. With the surface 14 abutting the eyelid 65, the main body 22 is displaced towards the eyelid 65. This displacement drives the plunger 12 and sensing device 32 into the body 22 (in the direction of arrow A). As the plunger 12 is displaced, pressure on the contact member 15 overcomes the counter pressure exerted on the plunger 12 by the coil spring 24.

This displacement continues, increasing the pressure on the contact member 15 until the user detects, within their eye, a spot or glow of light, or an arc of light, known as a pressure phosphene. The user then stops displacement of the body 22 and removes the tonometer 10 from the eye. The spring 26 will then displace the plunger 26 and the sensing device 32 out of the body 22 (in the direction of arrow B) and back to its initial position. The movement of the sensing member 32 both into and out of the body (indicated by arrow A and arrow B) generates a series of pulses, and the total pulse count is displayed on the display device 92, even after removal of the tonometer from the eye.

Figure 3:
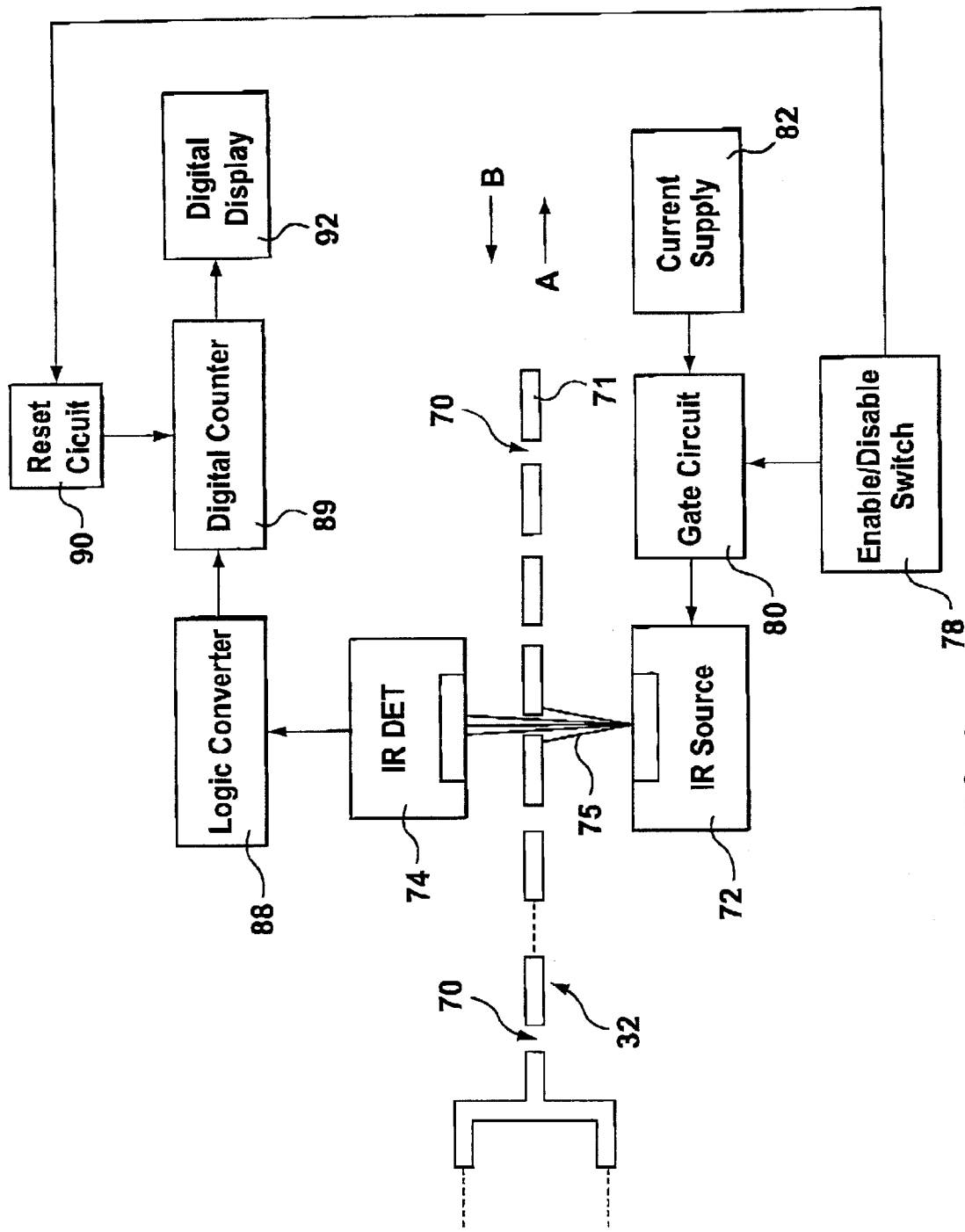
FIG. 3 illustrates a schematic view of a variant of the first embodiment of an electrical measurement apparatus shown in FIG. 2.

FIG. 3 shows an identical embodiment to that of FIG. 2, where the IR optical signal 75 passes through one of the slots 70 of the sensing member 32 and is received by the IR detector 74. In the embodiments shown in FIGS. 2 and 3, the pressure difference required to move the plunger 12 the distance between adjacent slots or holes 70 on the sensing member 32 depends on the strength of the coil spring 24. For a given intraocular pressure measurement, i.e. the pressure at which the pressure phosphene is detected, the displacement of the plunger 12 and consequently the sensing member 32 is determined from the number of pulses generated, and this displacement must be correlated with a calibrated intraocular pressure measurement. This is achieved by selecting an appropriate distance between slots or holes 70 on the sensing member 32. The calibration is done against Goldmann applanation tonometry, which is a standard test that compensates for variation in tissue rigidity in the eyelid and sclera. It will be appreciated that calibration may be done against other known tonometry methods or devices. Although the Goldmann tonometer may be used as a calibration tool, the Goldmann tonometer, in use is applied directly to the cornea of the patient. Hence, a skilled technision must carry out the procedure of measuring the intraocular pressure within a patient's eye.

Figure 4:
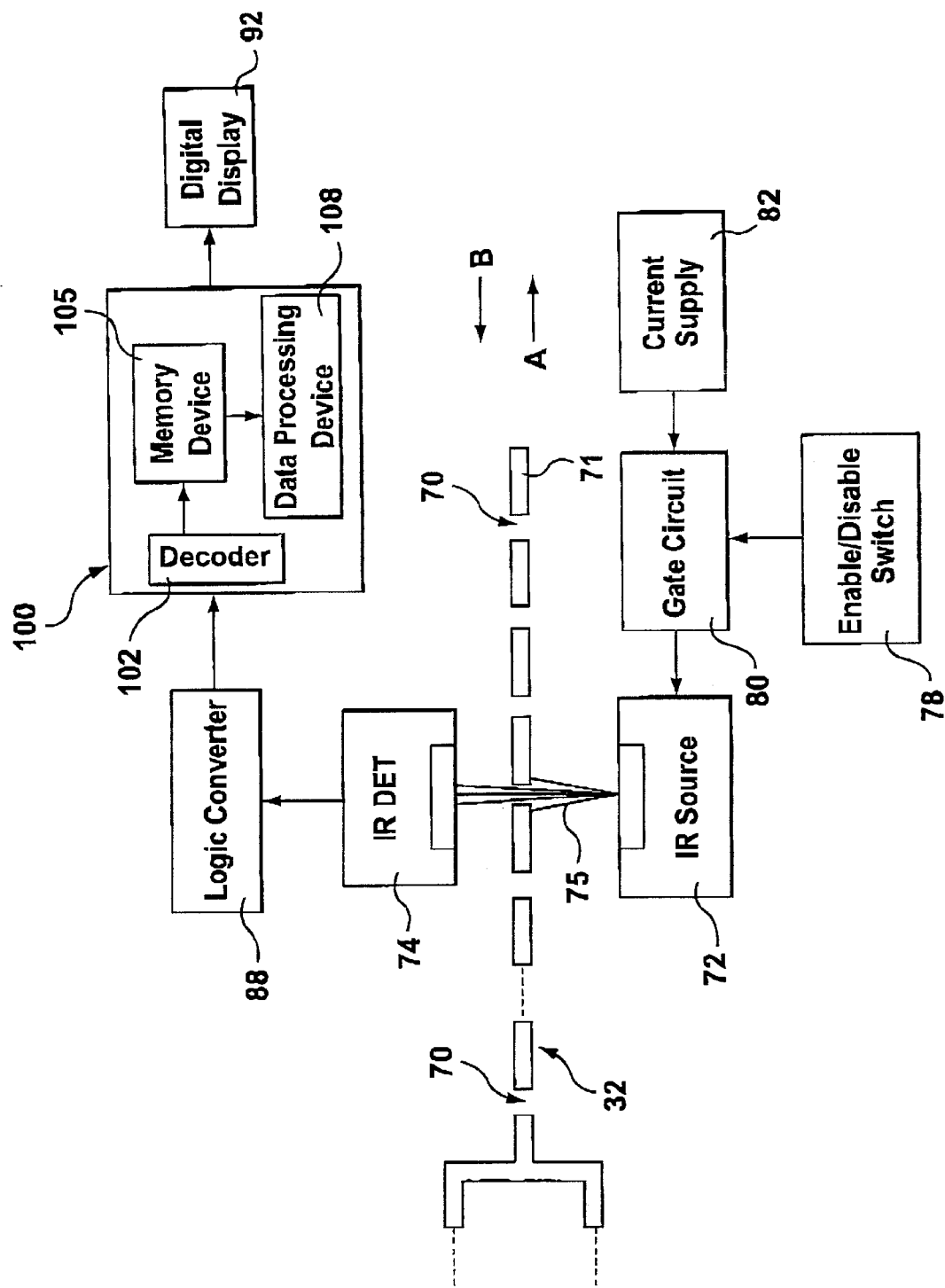
FIG. 4 illustrates a schematic view of a second embodiment of an electrical measurement apparatus of the tonometer of FIG. 1.

FIG. 4 shows an alternative embodiment of the present invention, where the electrical measurement apparatus 60 of the tonometer further comprises a programable logic device 100, which includes a decoder device 102, memory storage device 105 and data processing device 108.

In this aspect of the present invention, the distance between the slots or holes 70 on the sensing member 32 is made as small as possible. During intraocular pressure measurements, pressure is applied to the contact member 15 of the tonometer 10, displacing the sensing member 32 which causes pulses to be generated at the logic device 88 output. For a given number of generated pulses, the decoder 102 selects the correct calibrated pressure value which is stored in the memory device 105. The selected pressure value is sent to the digital display 92 and is stored in the data processing device 108 for producing measurement averages. The programmable logic device 100 allows the tonometer to be re-calibrated by reprogramming the logic device in order to make sure that the decoder assigns the correct pressure value for a given number of generated pulses. This is desirable due to measurement tolerances that may change as the coil spring 26 ages with use.

Referring to FIGS. 2,3 and 4, the distance between the slots 70 on the sensing device 32 must be smaller than the divergence angle of the IR optical signal, as defined by 75, emitted from the optical source 72. If the divergence angle of the IR optical signal , as defined by 75, is two wide, the IR detector will continuously detect the IR optical signal and the logic converter 88 will not generate pulses for incrementing the counter 89.

Figure 5:
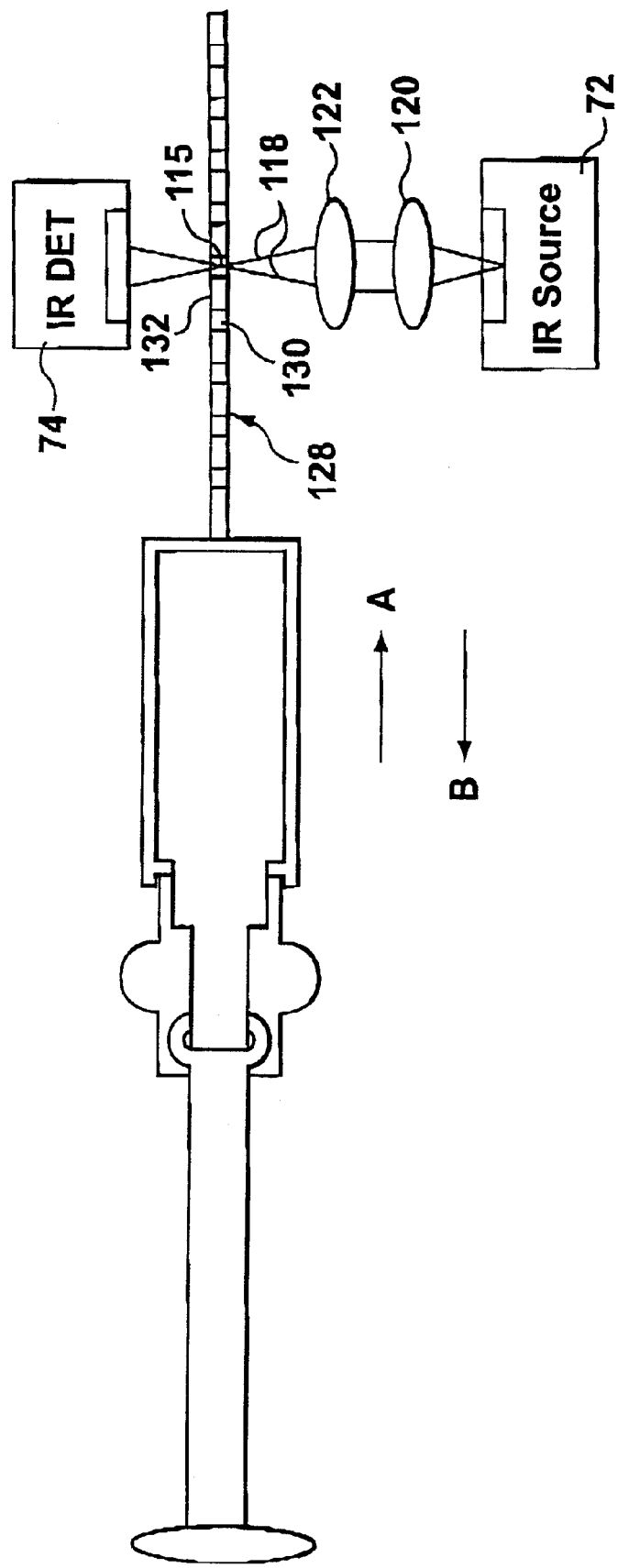
FIG. 5 illustrates the use of an optical coupling device for increasing the measurement resolution of an electrical measurement apparatus of a tonometer.

FIG. 5 illustrates a series of optical lenses for shaping the optical source's 72 optical signal 75, such that the optical beam, as indicated at 118, is incident on the sensing device as it converges into a focused spot, as indicated at 115. This ensures that for small slot sizes 130, the incident beam 118 is spatially confined within each slot 130 and blocking region 132 on the sensing device 128. It will be appreciated that optical lenses with dimensions in the region of a few millimeters can be used to implement this arrangement.

Figure 6:
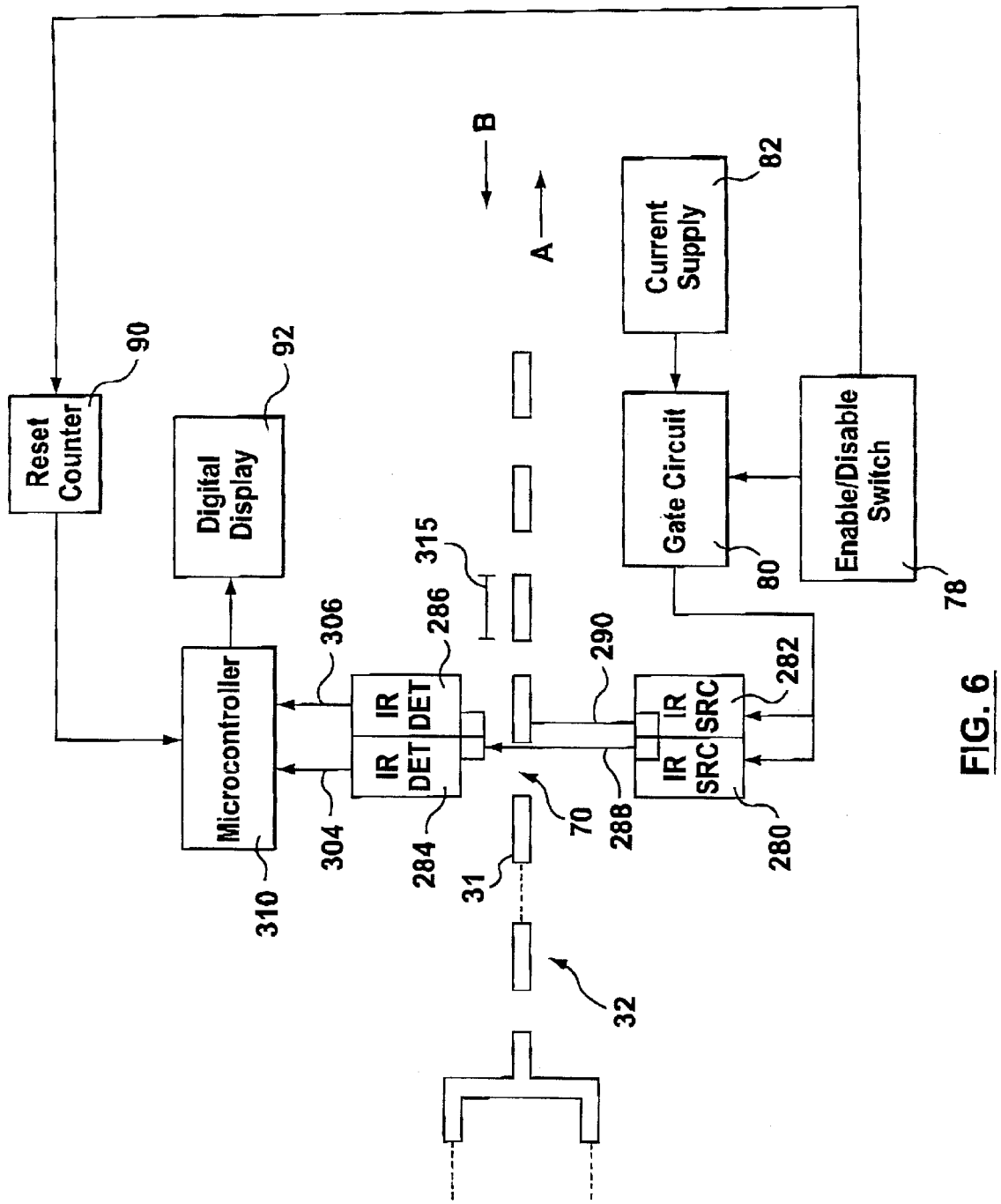
FIG. 6 illustrates a schematic view for a third embodiment of an electrical measurement apparatus of a tonometer.

FIG. 6 illustrates an alternative aspect of the present invention, where the electrical measurement apparatus 60 of the tonometer 10 illustrated in FIG. 1 comprises a microcontroller device 310. The microcontroller 310 processes a first and second electrical output 304, 306 received from a first and second Infra Red (IR) detector device 284, 286 respectively. The first and second Infra Red (IR) detector device 284, 286 detect first and second incident Infra Red (IR) optical signals 288, 290 transmitted from first and second optical Infra Red (IR) sources 280, 283 respectively. By providing a first and second incident optical signal 288, 290, the measurement resolution is increased for a given displacement of the sensing device 32.

The measurement resolution is increased by providing a lateral separation between the first and second incident optical signals 288, 290. The width of each slot 70 and the width of each blocking region 31 are the same, and this width is indicated at 315. Spacing the two optical signals 288, 290 by this distance 315 would give two similar pulse biases, one being the inverse of the other, with no increase in sensitivity. Instead, the lateral separation between the optical signals 288, 290 is approximately half the distance 315. This enables the microcontroller 310 to determine a minimum sensing device displacement of half the distance 315, so as to double the sensitivity. It will be appreciated that previous embodiments of the present invention which use a single optical source are limited to detecting a minimum sensing device displacement specified by the distance between alternate slot regions.

As illustrated in FIG. 6, the first optical signal 288 generated by the first optical source 280 passes through the slot region and is detected by the first detector 284. The second optical signal 290 generated by the second optical source 282 is blocked from the second detector 286 by the blocking region. This causes a logic high voltage (e.g. 5 V) to be present at the first electrical output 304 from the first detector 284, and a logic low (e.g. 0 V) to be present at the second electrical output 306 from the second detector 286. As the sensing device 32 is displaced by half the distance 315, the second optical signal 290 also passes through the slot region and is detected by the second detector 284. This causes a logic high voltage (e.g. 5 V) to be present at the second electrical output 306 as well as the logic high voltage (e.g. 0 V) already present at the first electrical output 304. As the sensing device 32 is further displaced by half the distance 315, the first optical signal 288 is blocked from the first detector 284 by the blocking region, whilst the second optical signal 290 continues to passes through the slot region and is detected by the second detector 286. This causes the logic high voltage (e.g. 5 V) to remain present at the second electrical output 306 and a logic low (e.g. 0 V) to appear at the first electrical output 304. As the sensing device 32 is again further displaced by the distance 315, the second optical signal 290 is also blocked from the second detector 286 by the blocking region, whilst the first optical signal 288 remains blocked. This causes a logic low voltage (e.g. 0 V) to appear at both the first electrical output 304 and second electrical output 306. The distance between two alternate slots or two alternate blocking regions is double the distance 315. By displacing the sensing member 32 by this distance, the first and second electrical outputs 304, 306 generate four combinations of output voltage variation. If a single optical source and detector were used (as in FIG. 2), the electrical output would generate only two output voltage variations for the same displacement of the sensing device. Hence the measurement resolution is doubled in the present embodiment (FIG. 6) which utilizes a pair of optical sources and detectors.

The alternate voltage changes at the first and second electrical outputs 304, 306 are processed by the microprocessor 310, whereby each alternate voltage change is processed as an incremental change in the displacement of the sensing device 32. Firmware is programmed into the microcontroller (not shown) for processing the electrical outputs 304, 306 from the detectors 284, 286 in order to generate a digitized representation of the pressure measurement based on this displacement of the sensing device 32. This digitized representation of the pressure measurement is received and displayed by a display device 92.

Figure 7:
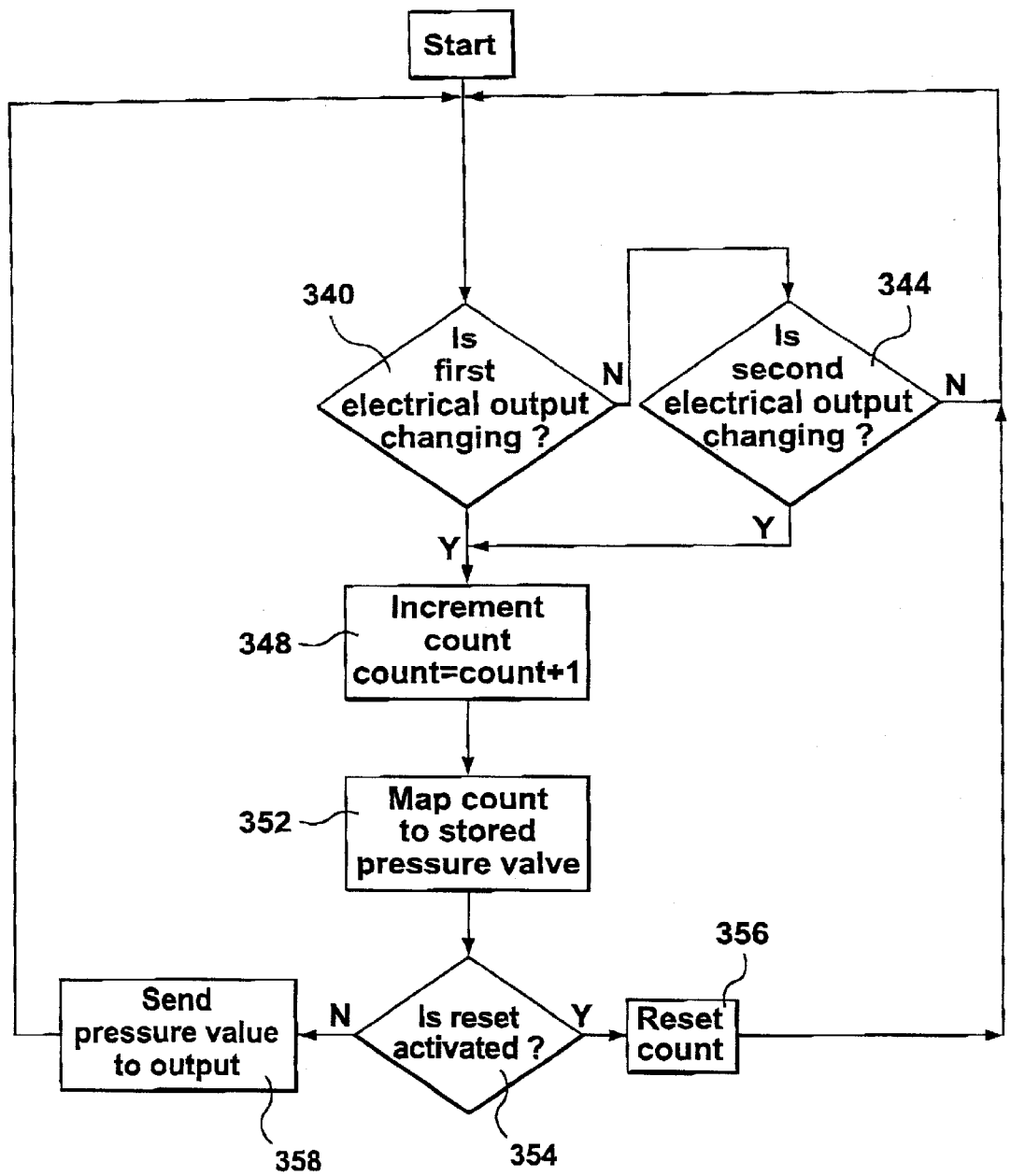
FIG. 7 illustrates a flow chart for the operation of a microcontroller device incorporated within a third embodiment of the electrical measurement apparatus of FIG. 6.

FIG. 7 shows a flow diagram representation of a typical functional representation for a Firmware programmed microcontroller 310. In a step 340, the first electrical output 304 is monitored in order to detect a voltage transition. Similarly, in a step 344, the second electrical output 306 is also monitored in order to detect a voltage transition. A voltage transition occurs when the first or the second electrical output signal (see FIG. 6, 304 and 306) changes from a logic high value (e.g. 5 V) to a logic low value (e.g. 0 V) or from a logic low value (e.g. 0 V) to a logic high value (e.g. 5 V). The first voltage transition from a logic high to a logic low occurs when the first or the second optical signal (see FIG. 6, 288 and 290) received by the first or second detector is blocked by the blocking region. Also, the second voltage transition from the a logic low to a logic high occurs when the blocking region is removed from the path of the first or the second optical signal (see FIG. 6, 288 and 290), such that the first or second detector receives the first or second optical signal. If in the step 340 or 344 a voltage transition is detected, the count value is incremented, as defined in a step 348, signifying an incremental displacement of the sensing device 32. The incremental displacement of the sensing device 32 is decoded and mapped to a corresponding pressure value, as defined in a step 352. If a reset has not been activated, as defined in a step 354, the pressure value determined in step 352 is output to a display, as defined in step 358 and the electrical outputs 304, 306 are once again monitored in steps 340 and 344. The first and second electrical outputs (304, 306) are continuously monitored until voltage transitions are detected and the count value is incremented and displayed. In a step 356, if the reset is activated, as defined in step 354, the count value is reset.

Figure 8:
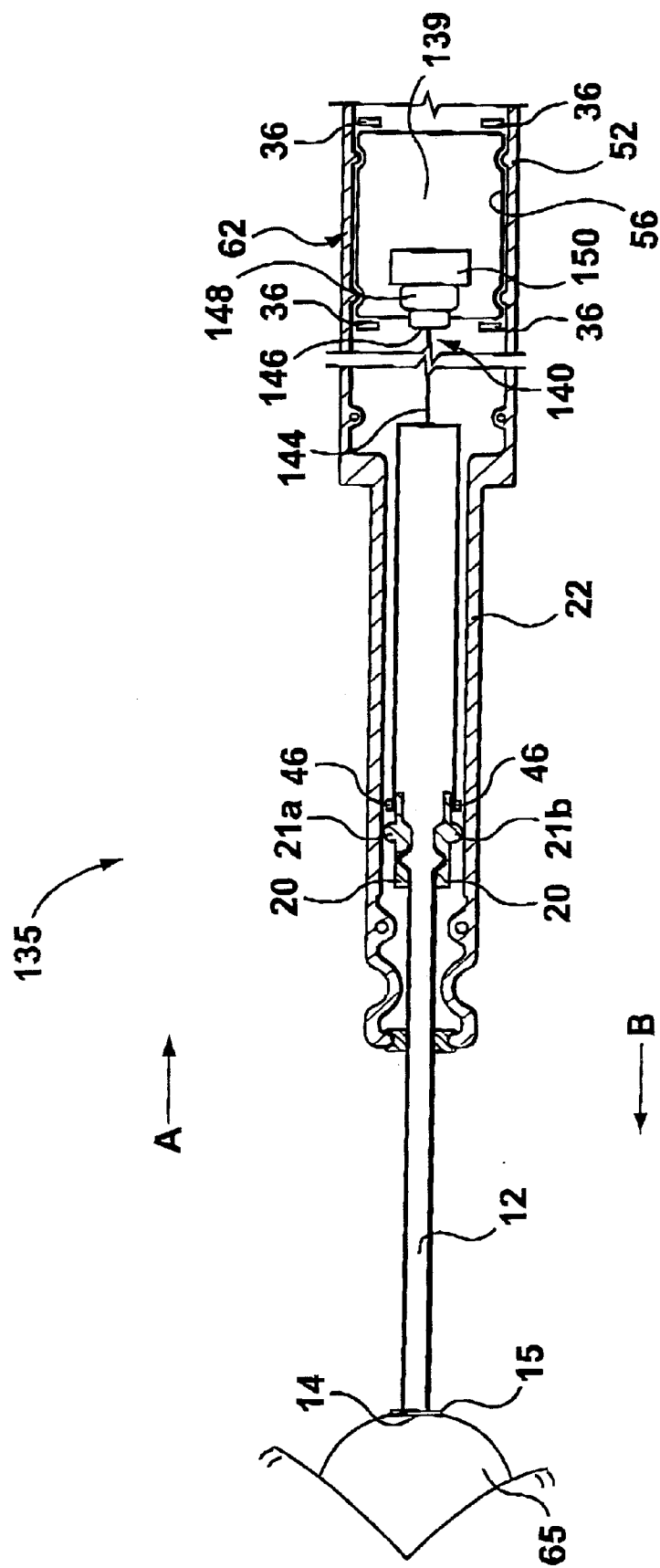
FIG. 8 illustrates a vertical cross sectional view of a second embodiment of a tonometer incorporating an electrical measurement apparatus.

In FIG. 8 and elsewhere, components common to FIG. 1 are given the same reference numerals. For simplicity and brevity, the description of these components is not repeated.

FIG. 8 shows an alternative embodiment of the present invention, wherein a sensing member 140 includes an extended rod 144 and an air filled balloon 148. The main body 22, plunger 12, and housing 62 of tonometer 135 are identical to tonometer 10 shown in FIG. 1. In this aspect of the present invention the extended rod 144 of sensing member 140 is attached at one end to the second bearing member 20 by means of a securing member 46. The other end of the rod 144 which extends into the housing cavity 56 includes a second contact member 146 which rests on the outer surface of the air filled balloon 148. By applying pressure to the plunger 12 and contact member 15, the plunger 12, the second bearing member 20 and the attached rod member 32 move into the body 22 and towards the housing 62. The second contact member 146 at the end of the rod member 144 compresses the air filled balloon member 148 in proportion to the inward pressure (see arrow A in FIG. 6) applied to the plunger 12. The compression of the air filled balloon member 148 is detected and processed by an electrical sensory and electrical processing circuitry 139 located within the housing cavity 56. It will be appreciated that in accordance with the present invention, the air filled balloon 148 can be replaced by any elastomer type material or foam material that regains it's original shape following compression and has a suitable eleastic modulus.

The electrical sensory and electrical processing circuitry 139 includes a pressure sensor device 150 which generates an electrical signal in proportion to the pressure exerted on the balloon member by the second contact member 146. The shape of the contact member 146 may be in the form of an annular disk or any other suitable shape.

A plurality of support legs 36 are used to mount a display device (not shown) on the surface of the tonometer 135 housing 62. The electrical signal from the electrical sensory and electrical processing circuitry 139 generates a read out of pressure on the display device in proportion to the applied pressure to the plunger 12 contact member 15.

By removing the pressure from the plunger 12 contact member 15, the outward force of compressed air within the air filled balloon 148 returns the plunger 12 to its original position by displacing the plunger out of the tonometer's body 22 (along the direction defined by arrow B).

The main body 22 may comprise two halves, wherein both halves are secured together by securing members 48 and 50. It will be appreciated that in accordance with the present invention, the securing members 48, 50 may include screws, snap on fittings or any other securing method for mating two complementary pieces. By removing the top half of the main body, access is provided to the electrical circuitry and mechanical components of the tonometer 135.

Figure 9:
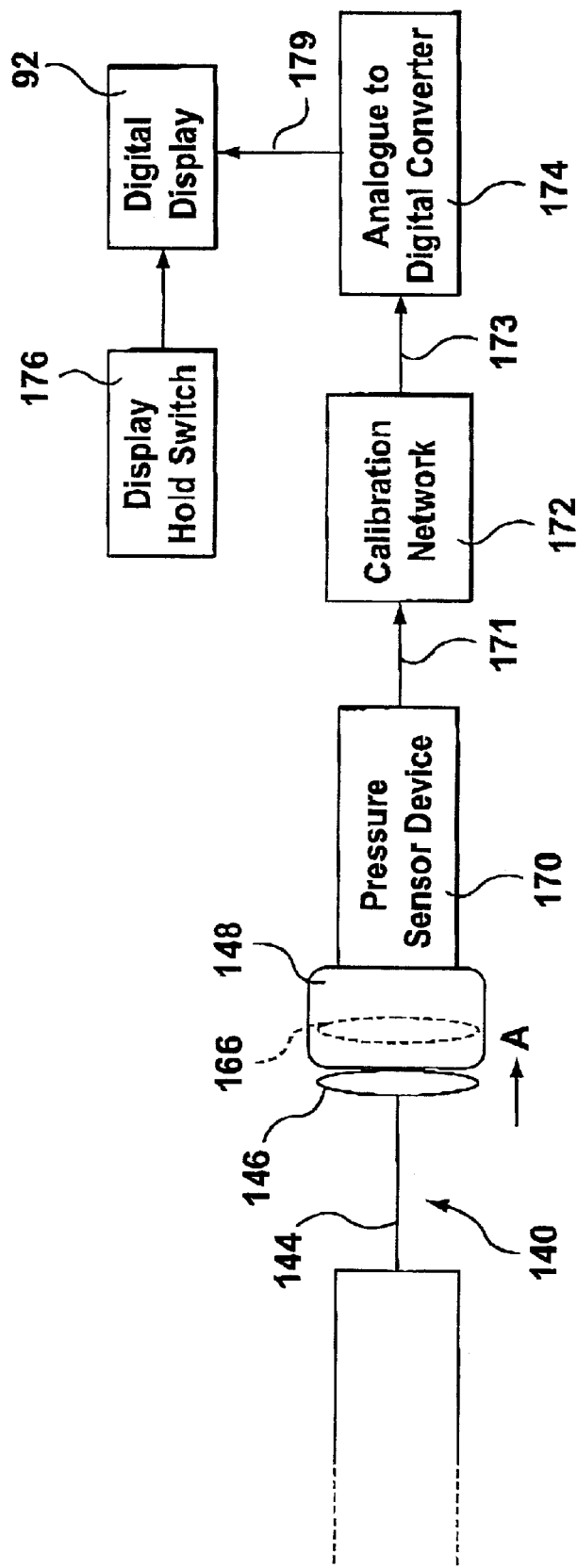
FIG. 9 illustrates a schematic view of a first embodiment of an electrical measurement apparatus of the tonometer of FIG. 8.

FIG. 9 illustrates a functional diagram of the electrical sensory and electrical processing circuitry 139 of the tonometer 135 shown in FIG. 8. As shown in FIG. 9, the air filled balloon 148 is placed on the surface of a pressure sensor device 170, where the pressure sensor device 170 may include a chip (e.g. SX or SLP series surface mount pressure sensors by SenSym) which generates an output voltage in proportion to the pressure applied to its surface. The second contact member 146 at the end of the rod member 144 compresses the air filled balloon 148 against the surface of the pressure sensor 170 in proportion to the inward pressure (direction of arrow A in FIG. 9) applied to plunger 12. The pressure applied to the surface of the pressure sensor 170 generates a pressure dependant output voltage 171 from the sensor 170, which is received by a calibration network 172. The calibration network 172 may include a variable gain amplifier and a network of passive components such as a resistor divider network. Depending on the magnitude of the pressure sensor device 170 output, the variable gain amplifier and resistor divider network are adjusted to generate a calibrated output on the tonometer display 92, which corresponds to a calibrated intraocular pressure measurement. The calibration is done against Goldmann applanation tonometry, which is a standard test that compensates for variation in tissue rigidity in the eyelid and sclera. It will be appreciated that calibration may be done against other known tonometry methods or devices.

The calibration network 172 output voltage 173 is converted to a digital signal 179 by means of an analog-to-digital convertor device 174. The digital signal 179 at the analog-to-digital convertor device 174 output is received by a digital display device 92 which holds the displayed value on the display once a display hold device 176 has been activated. De-activating the display hold causes the display 92 value to continuously receive the digital signal from the analog-to-digital convertor 174 output.

In use, the tonometer's 135 display hold device 176 is de-activated so the display 92 continuously displays the output from the analog-to-digital convertor 174.

Then, the contact member 15 (see FIG. 8) is brought up against the eyelid of a closed eye, this eyelid being indicated at 65. The contact member 15 is applied to the upper medial aspect of the eye, away from the cornea. This is done by the subject or user turning the eye outerwards and slightly downwards. Again, the eye may be either open or closed. The most convenient area may differ from person to person. The user just grasps the curved finger grip 44, to facilitate gripping of the device body 22 and places the circular surface 14 against the eyelid 65. With the surface 14 abutting the eyelid 65, the main body 22 is displaced towards the eyelid 65. This displacement drives the plunger 12 into the body 22, displacing the second contact member 146 at the end of the rod member 144 in the direction of arrow A. This causes the second contact member 146 to compresses the air filled balloon 148 against the surface of the pressure sensor 170 in proportion to the inward pressure (direction of arrow A in FIG. 8 and FIG. 9) applied to plunger 12.

The application of pressure on the contact member 15 causing displacement of the plunger 12 and compression of the pressure sensor 170 is continued until the user detects, within their eye, a spot or glow of light, or an arc of light, known as a pressure phosphene. The user then stops applying pressure on the contact member 15 and activates the display hold 176 prior to removing the tonometer 10 from the eye. As soon as the display hold 176 is activated, the measured pressure representing intraocular pressure is held on the display 92. Once the measured pressure value is stored on the display 92, applied pressure to the contact member 15 is removed by moving the tonometer 10 away from the eye 65. This causes the compressed air in the compressed balloon member 148 to apply an outward pressure on the second contact member which drives the plunger 12 out of the body 22 to its initial position.

Figure 10:
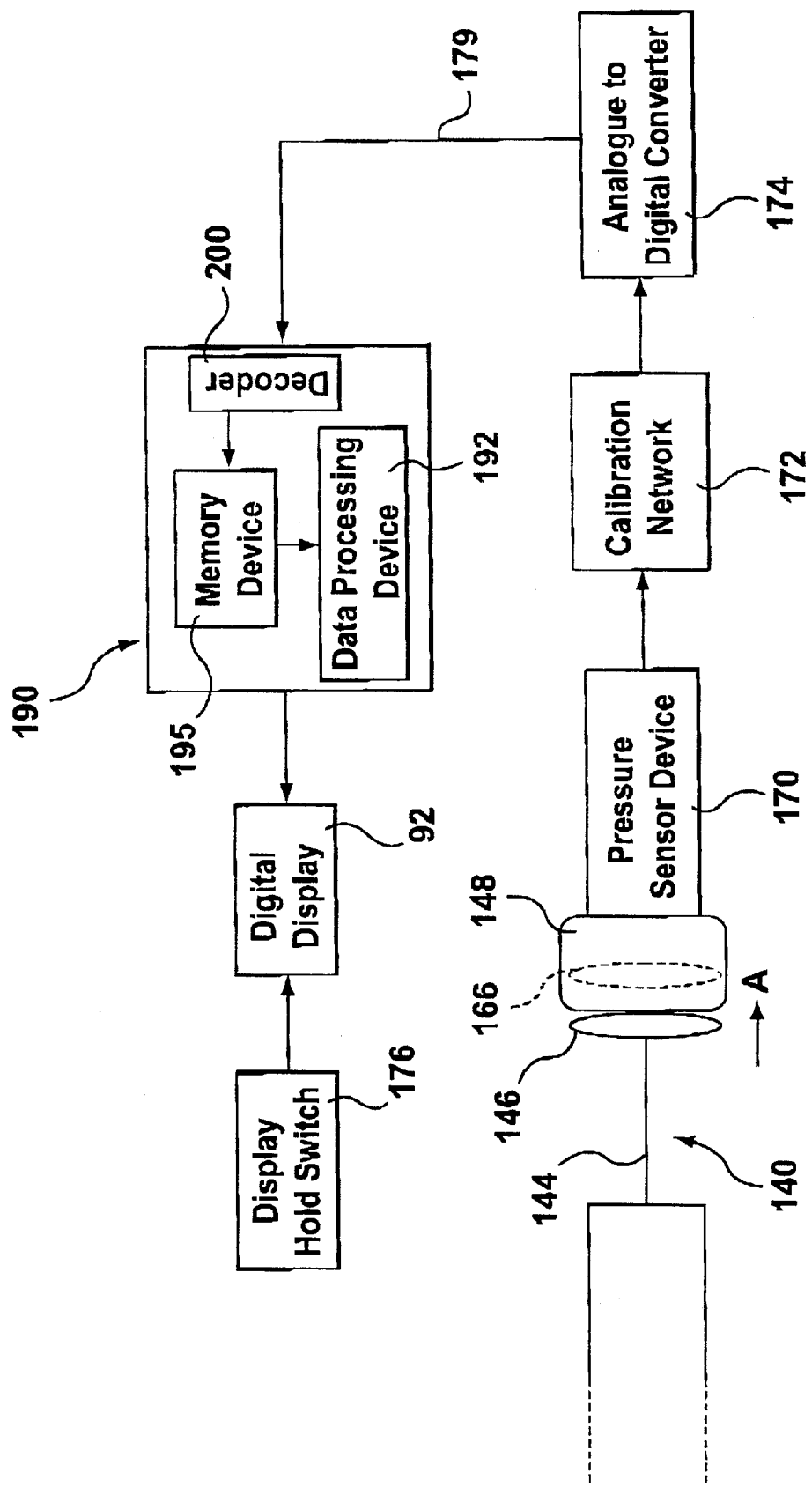
FIG. 10 illustrates a schematic view of a second embodiment of an electrical measurement apparatus of the tonometer of FIG. 8.

FIG. 10 shows an alternative embodiment of the functional diagram of the electrical sensory and electrical processing circuitry 139 illustrated in FIG. 9. As shown in FIG. 10, an additional programable logic device 190 receives the digitized pressure measurement from the analog-to-digital convertor output 179. The programmable logic device 190 includes a decoder device 200, memory storage device 195 and data processing device 192. The decoder 200 receives and decodes the analog-to-digital convertor output 179 value and selects the correct calibrated pressure value stored in the memory device 105. The selected pressure value is sent to the digital display 92 and is stored in the data processing device 192 for producing measurement averages. The programmable logic device 190 allows the tonometer to be re-calibrated by reprogramming the logic device in order to make sure that the decoder 200 assigns the correct intraocular pressure value for a given pressure output from the pressure sensor device 170. This is desirable due to measurement tolerances that may change with mechanical wearing of the tonometer's components 135.

It will be appreciated that most of the components within the electrical measurement apparatus of the present invention are commercially available in surface mount packaging, and therefore suitable for use within the limited space of the tonometer housing 52.

Figure 11:
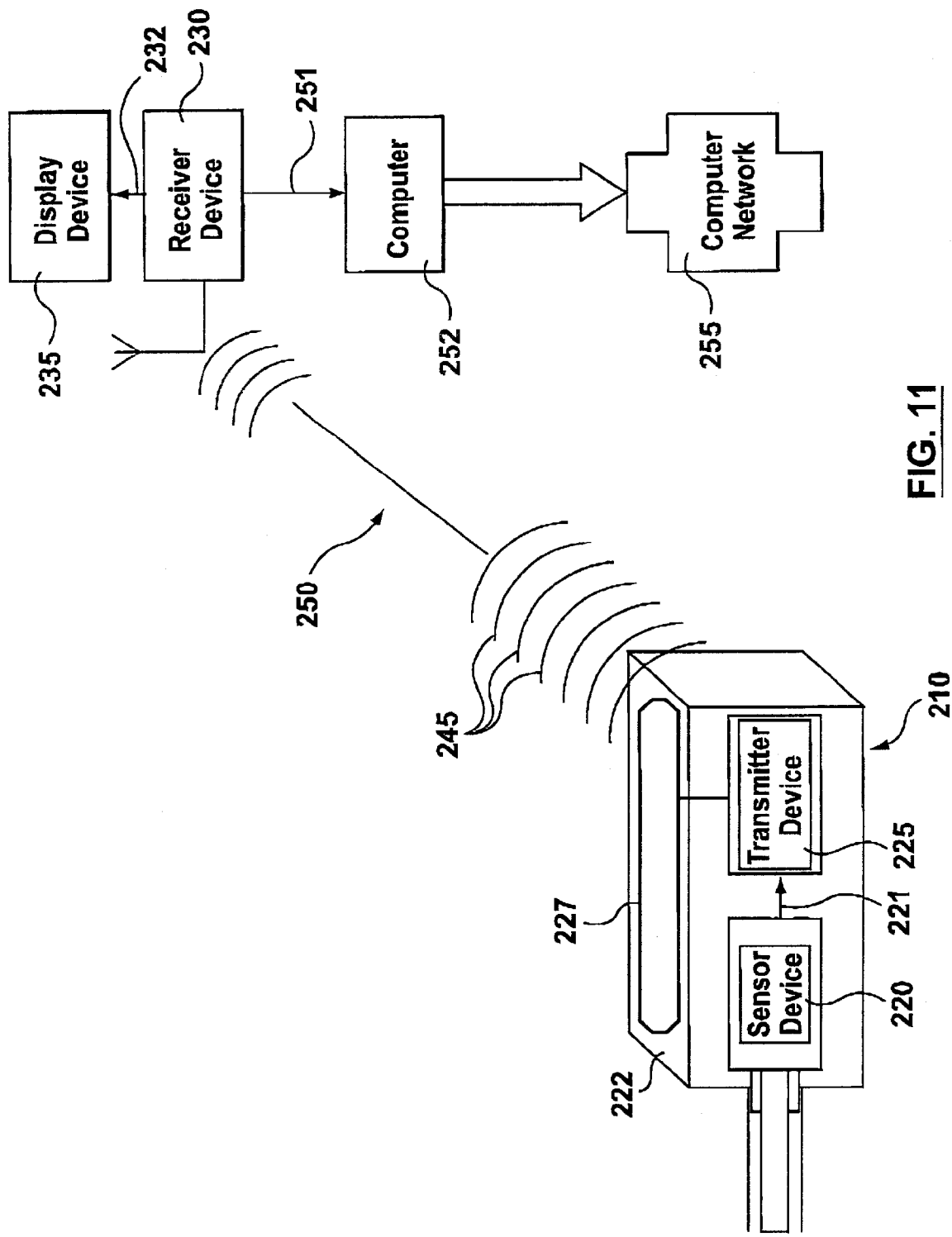
FIG. 11 illustrates a telemetry device incorporated within a tonometer.

In yet another alternative embodiment of the present invention, a telemetry device may be incorporated into the electrical measurement apparatus of the tonometer 10, 135 (FIGS. 1 and 8). As shown in FIG. 11, the tonometer 210 comprises a telemetry device which includes a transmitter device 225 and an antenna device 227 built into the outer casing 222. The transmitter device 225 receives an output signal 221 from the sensor device 220 and transmits the output signal 221 over the communication link, as defined by 250, via the antenna 227. The antenna 227 radiates a transmission signal 245 to a corresponding antenna of a remote receiver device 230, where the sensor output signal 221 is recovered and processed accordingly. The recovered sensor output signal 232 is sent to a display device 235, where the recovered output signal 232 is displayed in suitable format. The display format may be in digital form or in the form of a graph representing consecutive intraocular pressure measurements. It will be appreciated that the transmitter device may incorporate various wireless communication solutions such as a short range (no licence requirements) UHF transmitter device (e.g. FRM TX6000 Hybrid Transmitter using OOK and ASK modulation) or an Infra Red transmitter. The receiver device 230 is also capable of generating an output interface signal 251 which is received by a computer 252 and transmitted over the computer network 255 to a suitable recipient (e.g. an optometrist).

The embodiments of the present invention provide an applanation tonometer with integrated electrical processing circuitry for providing an electrical read out of intraocular pressure. It should be understood that various modifications can be made to the preferred and alternative embodiments described and illustrated herein, the scope of which is defined in the appended claims.

I claim:

1. An applanation tonometer, for measuring pressure within an eye, the tonometer comprising:
   (a) a main body;
   (b) a plunger mounted in the main body for movement relative thereto and having a first end portion comprising a contact member for contacting an eyelid, the contact member being substantially planar and sufficiently large that, in use, the eyeball is flattened and subjected to applanation, and the plunger having a second end portion mounted in the main body;
   (c) a transducer mounted between the plunger and the main body, for converting a load applied to the first end portion of the plunger into an electrical signal;
   (d) an electrical display device connected to the transducer, for indicating the magnitude of the load applied to the first end portion of the plunger;
wherein the plunger is slidably mounted within the main body;
wherein a spring member is mounted between the plunger and the main body for providing a spring biasing force in relation to the displacement of the plunger relative to the main body, wherein the transducer includes a sensing device attached to the plunger, for conversion of the displacement of the plunger into the electrical signal, wherein the sensing device comprises an elongate member provided with a plurality of slot regions, and a plurality of blocking regions, alternating with one another, and wherein the transducer includes measurement means provided at a measurement location, for counting blocking regions and slot regions passing by the measurement location.

2. A tonometer as claimed in claim 1, which includes bearing members between the plunger and the main body.

3. The tonometer as claimed in claim 2, wherein the plunger is generally tubular and wherein the main body includes a first portion that is generally tubular, and wherein the bearing members comprise first and second annular bearing members provided between the tubular portion of the main body and the plunger.

4. A tonometer as claimed in claim 3, wherein the first portion of the main body includes inwardly curved fingered grip portions on the first portion thereof.

5. A tonometer as claimed in claim 1, wherein the transducer comprises:
   (a) a sensing device attached to the plunger, the sensing device comprising a plurality of slot regions and plurality of blocking regions alternating with one another;
   (b) an optical source for generating an optical signal, the optical signal incident on the sensing device, wherein the blocking regions of the sensing device block the optical signal incident on the sensing device and the slot regions of the sensing device pass the optical signal incident on the sensing device;
   (c) an optical detector comprising an optical input and an electrical output, wherein the optical detector receives the optical signal on the optical input and generates an electrical signal at the electrical output;
   (d) a logic convertor device which converts the electrical output signal from the optical detector to a plurality of pulse signals; and
   (e) a digital counter device for receiving the plurality of pulse signals and generating an output count value, wherein each of the plurality of pulse signals increment the output count value;
wherein the electrical display device receives and displays the output count value from the digital counter, the count value corresponding to the magnitude of applied pressure to the contact member.

6. A tonometer as claimed in claim 5, wherein the optical detector provides one output when an optical signal is sensed indicative of the presence of one of the slot regions and another output when no optical signal is sensed, indicative of a presence of one of the blocking regions, the first and second outputs being distinct from one another whereby the logic converter is able to convert the electrical output of the optical detector to a plurality of pulse signals.

7. A tonometer as claimed in claim 6, wherein the first and second outputs of the optical detector are such as to generate a series of electrical pulses.

8. A tonometer as claimed in claim 5, which further includes an optical coupling device, coupling the optical signals for the sensing device.

9. A tonometer as claimed in claim 8, wherein the optical coupling device includes:
   (a) a collimating lens, the collimating lens having an input and an output, whereby the collimating lens receives the incident optical signal at the input and generates a collimated optical signal at the output; and
   (b) a focusing lens, wherein the focusing lens receives the collimated optical signal from the output and generates a focused optical signal onto the sensing device.

10. A tonometer as claimed in claim 1, wherein the transducer comprises:
   (a) a sensing device attached to the plunger, the sensing device comprising a plurality of slot regions and plurality of blocking regions alternating with one another;
   (b) an optical source for generating an optical signal, the optical signal incident on the sensing device, wherein the blocking regions of the sensing device block the optical signal incident on the sensing device and the slot regions of the sensing device pass the optical signal incident on the sensing device;
   (c) an optical detector comprising an optical input and an electrical output, wherein the optical detector receives the optical signal on the optical input and generates an electrical signal at the electrical output;
   (d) a logic convertor device connected to the optical detector for converting the electrical output signal from the optical detector to a plurality of pulse signals; and
   (e) a programmable logic device for receiving the plurality of pulse signals and generating a digitized pressure value;
wherein the electrical display device receives and displays the digitized pressure values from the programmable logic device, the digitized pressure values corresponding to the magnitude of applied pressure to the contact member.

11. A tonometer as claimed in claim 10, wherein the programmable logic device compromises:
   (a) a decoder device for receiving the plurality of pulse signals from the logic convertor and generating a decoder output signal;
   (b) a memory device connected to the decoder device for receiving the decoder output signal, wherein the memory device processes the decoder output signal and retreives the digitized pressure values from a designated memory location within the memory device; and
   (c) a data processing device connected to the memory device wherein the data processing device generates average digitized pressured values based on a series of digitized pressure values received from the memory device;
wherein the device receives both the digitized pressure values from the memory device and the average digitized pressure values from the data processing device.

12. The tonometer as claimed in claim 1, wherein the transducer comprises:
   (a) a sensing device comprising a plurality of slot regions and a plurality of blocking regions alternating with one another;
   (b) a first optical source for generating a first optical signal, the first optical signal incident on the sensing device, and a second optical source for generating a second optical signal, the second optical signal incident on the sensing device, wherein the blocking regions of the sensing device block the first and second optical signal incident on the sensing device, and the slot regions of the sensing device pass the first and second optical signal incident on the sensing device;
   (c) a first optical detector comprising a first optical input and a first electrical output, wherein the first optical detector receives the first optical signal on the first optical input and generates a first electrical signal at the first electrical output;

(d) a second optical detector comprising a second optical input and a second electrical output, wherein the second optical detector receives the second optical signal on the second optical input and generates a second electrical signal at the second electrical output; and (e) a microcontroller having a first electrical input and a second electrical input receiving the first electrical signal from the first detector, and the second electrical input receiving the second electrical signal from the second detector, wherein the microcontroller processes the first and second electrical signal, and generates a corresponding digitized pressure value;

wherein the electrical display device receives and displays the digitized pressure value from the microcontroller, the digitized pressure value corresponding to the magnitude of applied pressure to the contact member.

13. A tonometer as claimed in claim 12, wherein the first and second electrical signals comprise first and second series of electrical pulses and wherein the first electrical input of the microcontroller receives the first series of electrical pulses from the first optical detector, and the second electrical input of the microcontroller receives the second series of electrical pulses from the second optical detector, the microcontroller compares each pulse corresponding to both the first series of electrical pulses and the second series of electrical pulses, and if each pulse corresponding to the first series of electrical pulses or the second series of electrical pulses makes a first voltage transition or a second voltage transition, then the microcontroller increments an internal counter which generates a digitized count value, wherein the count value provides a means for selecting the corresponding digitized pressure value based on the magnitude of applied pressure to the contact member.

14. A tonometer as claimed in claim 13, wherein the first voltage transition is a voltage change from a logic high value to a logic low value, the logic high value being a voltage in the range of 2.5 to 5 volts and a logic low value being a voltage in the range of 0 to 1 volts; and the second voltage transition is a voltage change from a logic low value to a logic high value, the logic low value being a voltage in the range of 0 to 1 volts and the logic high value being a voltage in the range of 2.5 to 5 volts.

15. A tonometer as claimed in claim 14, further comprising: a first optical coupling device for coupling the first optical signal to the sensing device; and a second coupling device for coupling the second optical signal to the sensing device.

16. A tonometer as claimed in claim 15, wherein the first optical coupling device and second optical coupling device both include:

(a) a collimating lens, the collimating lens having an input and an output, whereby the collimating lens receives the incident optical signal at the input and generates a collimated optical signal at the output; and (b) a focusing lens, wherein the focusing lens receives the collimated optical signal from the output and generates a focused optical signal onto the sensing device.

17. A tonometer as claimed in claim 1, wherein the transducer includes a memory device for storing the magnitude of the maximum load detected by the tonometer, and means for coupling the tonometer to an external data processing device.

18. A tonometer as claimed in claim 1 or 17, which includes a transmitter within the tonometer for wireless transmission of data from the tonometer to an external data processing device.

* * * * *